United States Patent [19]

Scolnick

[11] Patent Number: 5,663,195

[45] Date of Patent: Sep. 2, 1997

[54] METHOD OF PREVENTING BONE LOSS

[75] Inventor: Edward M. Scolnick, Wynnewood, Pa.

[73] Assignee: Merck & Co., Inc., Rahway, N.J.

[21] Appl. No.: 646,604

[22] Filed: May 8, 1996

Related U.S. Application Data

[63] Continuation of Ser. No. 325,759, Oct. 19, 1994, abandoned.

[51] Int. Cl.$^6$ .................................................... A61K 31/34
[52] U.S. Cl. ............................................................ 514/461
[58] Field of Search ................................................ 514/461

[56] References Cited

U.S. PATENT DOCUMENTS

| 4,921,697 | 5/1990 | Peterlik et al. | 424/85.5 |
| 5,474,995 | 12/1995 | Ducharme et al. | 514/241 |

FOREIGN PATENT DOCUMENTS

| 2 283 745 | 5/1995 | United Kingdom . |
| WO94/13635 | 6/1994 | WIPO . |
| WO94/15932 | 7/1994 | WIPO . |
| WO94/26731 | 11/1994 | WIPO . |
| WO95/21817 | 8/1995 | WIPO . |

OTHER PUBLICATIONS

B. J. Votta, et al., Bone, vol. 15, No. 5, pp. 533–538 (1994) "Cytokine Suppressive Anti–inflammatory Compounds Inhibit Bone Resorption In Vitro".

E. M. Lemmel, Eur. J. Clin. Pharmacol., vol. 47, No. 1, Abstract A52, (1994).

N. H. Bell, et al., Am. Journ. of Med., vol. 96, pp. 349–353 (Apr., 1994) "Diclofenac Sodium Inhibits Bone Resorption in Postmenopausal Women".

N. Lane, et al., Journ. of Bone and Mineral Research, vol. 6, No. 10, pp. 1029–1035 (1990) "Effect of Naproxen on Cancellous Bone in Ovariectomized Rats".

R.T. Turner, et al., Endocrinology, vol. 122, No. 3, pp. 1146–1150 (1988) "Tamoxifen Inhibits Osteoclast–Mediated Resorption of Trabecular Bone on Ovarian Hormone–Deficient Rats".

*Primary Examiner*—Theodore J. Criares
*Attorney, Agent, or Firm*—Curtis C. Panzer; David L. Rose

[57] ABSTRACT

The invention encompasses a method of inhibiting bone resorption in patients in need of such inhibition to a degree sufficient to halt or retard loss of bone mass, reduce fractures, improve bone repair and prevent or treat osteoporosis comprising: the administration of a non-toxic therapeutically effective amount of a selective cyclooxygenase-2 inhibitor such as the compounds of formula I.

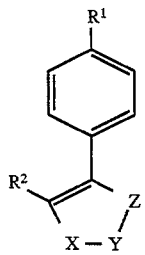

The invention also encompasses certain pharmaceutical compositions for the purposes described above.

15 Claims, No Drawings

METHOD OF PREVENTING BONE LOSS

This is a continuation of application Ser. No. 08/325,759 filed Oct. 19, 1994, now abandoned.

BACKGROUND OF THE INVENTION

The invention relates to a method of inhibiting bone resorption, halting or retarding loss of bone mass, reducing fractures, improving bone repair and preventing or treating osteoporosis, particularly in post-menopausal women. Treatment of additional diseases/disorders is also disclosed.

The current major bone diseases of public concern include osteoporosis (post-menopausal, idiopathic and secondary to immobilization or drugs such as glucocorticoids), bone lesions due to metastases, hypercalcemia of malignancy, oral bone loss due to periodontal disease, hyperparathyroidism, periarticular erosions in rheumatoid arthritis and Paget's disease.

All these conditions are characterized by bone loss, resulting from an imbalance between bone resorption (breakdown) and bone formation. This process of bone remodeling or bone turnover continues throughout life and replaces about 14% of the skeletal mass per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12–20% mortality rate within the first two years, while over 30% of the patients require nursing home care after the fracture.

Individuals suffering from all the conditions listed above would benefit from treatment with agents which inhibit bone resorption.

There is evidence in the literature that prostaglandins act as modulators of the bone resorption process. There is also evidence that certain non-steroidal anti-inflammatory agents (NSAID's) may (to some degree) reduce bone resorption. See, for example, the reports on the use of Diclofenac sodium by post menopausal women (*Am. J. Medicine*, Vol. 96, pp. 349–353, 1994); naproxen (*J. Bone Mineral Res.*, Vol. 5, pp. 1029–1035, 1990) in laboratory animal models.

As is appreciated by those of skill in the art, the natural processes of bone resorption and bone renewal are in constant dynamic equilibrium. This equilibrium, however, may differ with time (age), sex, and/or hormonal balance. Accordingly, the existence of evidence supporting the premise that the administration of an NSAID to post-menopausal women, may (to some degree) retard bone resorption, can not be taken as an indicator that the administration of NSAID's will affect a sufficient shift in equilibrium to halt or retard loss of bone mass, reduce fractures, improve bone repair or provide an effective means of preventing or treating osteoporosis. See in contrast GB 2,118,042 issued Jan. 15, 1986 (U.S. Pat. No. 4,621,077), which discloses the use of bisphosphonates, including alendronate, which have been shown effective in the prevention of bone loss in post-menopausal women.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase has been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, evidence is mounting that the constitutive enzyme, cyclooxygenase-1, is responsible, in large part, for endogenous basal release of prostaglandins and hence is important in their physiological functions such as the maintenance of gastrointestinal integrity and renal blood flow. In contrast, the inducible form, cyclooxygenase-2, appears to be mainly responsible for the pathological effects of prostaglandins where rapid induction of the enzyme would occur in response to such agents as inflammatory agents, hormones, growth factors, and cytokines.

Surprisingly, the applicant has now found that selective cyclooxygenase-2 inhibitors, and in particular the compounds of formula I as described below are effective in inhibiting bone resorption, halting or retarding loss of bone mass, reducing fractures, improving bone repair and preventing or treating osteoporosis.

SUMMARY OF THE INVENTION

The invention encompasses a method of inhibiting bone resorption in patients in need of such inhibition to a degree sufficient to halt or retard loss of bone mass, reduce fractures, improve bone repair and prevent or treat osteoporosis comprising: the administration of a non-toxic therapeutically effective amount of a selective cyclooxygenase-2 inhibitor such as the compounds of formula I.

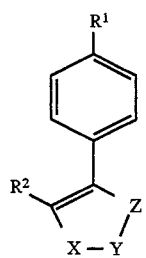

The invention also encompasses the treatment of additional diseases and disorders as disclosed herein.

The invention also encompasses pharmaceutical compositions for the purposes described herein.

DETAILED DESCRIPTION OF THE INVENTION

The invention encompasses a method of inhibiting bone resorption in patients in need of such inhibition to a degree sufficient to either prevent, retard, halt or reverse loss of bone mass, thereby reducing the risk of fractures, comprising: the administration of a non-toxic therapeutically effective amount of a selective cyclooxygenase-2 inhibitor such as the compounds of Formula I

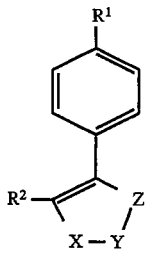

or a pharmaceutically acceptable salt thereof wherein:
X—Y—Z— is selected from the group consisting of:
(a) —$CR^5(R^{5'})$—O—C(O)—,
(b) —C(O)—O—$CR^5(R^{5'})$—, $R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$, $R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl or naphthyl wherein the substituent is selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^3)(R^4)$—OH,
(12) —$C(R^3)(R^4)$—O—$C_{1-4}$alkyl, and
(13) —$C_{1-6}$alkyl-$CO_2$—$R^3$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additionally N atoms; or the heteroaryl is a monocyclic ring of 6 atoms, said ring having one hetero atom which is N, and optionally 1, 2, 3, or 4 additional N atoms; said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^3)(R^4)$—OH, and
(10) —$C(R^3)(R^4)$—O—$C_{1-4}$alkyl;
(e) benzoheteroaryl which includes the benzo fused analogs of (d);

$R^3$, $R^4$, $R^5$ and $R^{5'}$ are each independently selected from the group consisting of (a) hydrogen,
(b) $C_{1-6}$alkyl.

For purposes of this specification a compound shall be defined as a selective cyclooxygenase-2 inhibitor if the ratio of it's $IC_{50}$ for the inhibition of cyclooxygenase-1 divided by it's $IC_{50}$ for the inhibition of cyclooxygenase-2, as measured as described in this specification or a comparable method is 200 or greater; preferably 1000 or greater. Accordingly, other selective cyclooxygenase-2 inhibitors within the scope of the invention include:

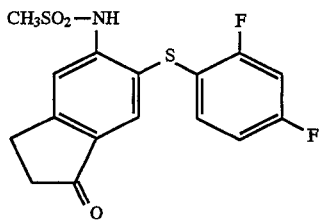

and other specific inhibitors discloses in WO 94/13635, published Jun. 23, 1994; U.S. Pat. No. 5,344,911, issued Sep. 6, 1994; and WO 94/15932, published Jul. 21 1994, all of which are hereby incorporated by reference.

In one genus the invention is directed to a method of preventing or treating osteoporosis, particularly in (but not limited to) post-monopausal women.

In a second genus the invention is directed to a method of inhibiting bone resorption in patients in need of such inhibition to a degree sufficient to substantially halt a loss of bone mass.

In a third genus the invention is directed to a method of reducing fractures in post-menopausal women or other patients who have suffered bone loss or have osteoporosis.

In a fourth genus the invention is directed to a method of maintaining bone density in post-menopausal women or other patients who susceptible to bone loss or have suffered bone loss or have osteoporosis.

Highly specific cyclooxygenase-2 inhibitors, such as compounds of formula I are also useful in the treatment of hypercalcemia of malignancy, osteolysis due to bone metastases, oral bone loss due to periodontal disease, hyperparathyroidism, periarticular erosions in rheumatoid arthritis, Paget's disease, and secondary forms of osteoporosis such as immobilization-induced osteoporosis and osteoporosis resulting from glucocorticoid treatment, hyperthyroidism and thyroid hormone ($T_3$, $T_4$) treatment.

Each of these categories embraces the use of compounds of Formula Ia

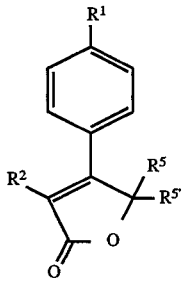

or pharmaceutically acceptable salts thereof wherein:
$R^1$ is selected from the group consisting of
(a) $S(O)_2CH_3$,
(b) $S(O)_2NH_2$,
(c) $S(O)_2NHC(O)CF_3$,
(d) $S(O)NHCH_3$, (e) S(O)NHNH$_2$, and
(f) S(O)NHNHC(O)CF$_3$;

R$^2$ is selected from the group consisting of
(a) C$_{1-6}$alkyl,
(b) C$_3$, C$_4$, C$_5$, C$_6$, and C$_7$, cycloalkyl,
(c) mono- or di-substituted phenyl wherein the substituent is selected from the group consisting of
  (1) hydrogen,
  (2) halo,
  (3) C$_{1-6}$alkoxy,
  (4) C$_{1-6}$alkylthio,
  (5) CN,
  (6) CF$_3$,
  (7) C$_{1-6}$alkyl,
  (8) N$_3$,
  (9) —CO$_2$H,
  (10) —CO$_2$—C$_{1-4}$alkyl,
  (11) —C(R$^3$)(R$^4$)—OH,
  (12) —C(R$^3$)(R$^4$)—O—C$_{1-4}$alkyl, and
  (13) —C$_{1-6}$alkyl—CO$_2$—R$^3$;
(d) heteroaryl
(e) benzoheteroaryl R$^3$, R$^4$, R$^5$ and R$^{5'}$ are each independently selected from the group consisting of
(a) hydrogen,
(b) C$_{1-6}$alkyl.

Within this class is the sub-class of compounds of Formula Ia wherein

R$^1$ is selected from the group consisting of
(a) S(O)$_2$CH$_3$,
(b) S(O)$_2$NH$_2$,
(c) S(O)$_2$NHC(O)CF$_3$,
(d) S(O)NHCH$_3$,
(e) S(O)NHNH$_2$, and
(f) S(O)NHNHC(O)CF$_3$;

R$^2$ is selected from the group consisting of
(a) C$_{1-4}$alkyl,
(b) C$_3$, C$_4$, C$_5$, C$_6$, and C$_7$, cycloalkyl,
(c) mono- or di-substituted phenyl wherein the substituent is selected from the group consisting of
  (1) hydrogen,
  (2) fluoro, chloro, and bromo,
  (3) C$_{1-4}$alkoxy,
  (4) C$_{1-4}$alkylthio,
  (5) CN,
  (6) CF$_3$,
  (7) C$_{1-4}$alkyl,
  (8) N$_3$,
  (9) —CO$_2$H,
  (10) —CO$_2$—C$_{1-3}$alkyl,
  (11) —C(R$^3$)(R$^4$)—OH, and
  (12) —C(R$^3$)(R$^4$)—O—C$_{1-3}$alkyl,
(d) mono- or di-substituted heteroaryl selected from the group consisting of
  (1) furanyl,
  (2) diazinyl, triazinyl and tetrazinyl,
  (3) imidazolyl,
  (4) isooxazolyl,
  (5) isothiazolyl,
  (6) oxadiazolyl,
  (7) oxazolyl,
  (8) pyrazolyl,
  (9) pyrrolyl,
  (10) thiadiazolyl,
  (11) thiazolyl,
  (12) thienyl,
  (13) triazolyl, and
  (14) tetrazolyl,
  wherein said substituents are selected from the group consisting of
  (a) hydrogen,
  (b) fluoro, chloro, bromo;
  (c) C$_{1-4}$alkoxy,
  (d) C$_{1-4}$alkylthio,
  (e) CN,
  (5) CF$_3$,
  (6) C$_{1-4}$alkyl,
  (7) N$_3$,
  (8) —C(R$^3$)(R$^4$)—OH,
  (9) —C(R$^3$)(R$^4$)—O—C$_{1-4}$alkyl.

Within this sub-class is the group of compounds of Formula Ia wherein

R$^2$ is selected from the group consisting of
(a) cyclohexyl, and
(b) mono- or di-substituted phenyl, and wherein the substituents are selected from the group consisting of
  (1) hydrogen,
  (2) halo,
  (3) C$_{1-4}$alkoxy,
  (4) C$_{1-4}$alkylthio,
  (5) CN,
  (6) CF$_3$,
  (7) C$_{1-4}$alkyl,
  (8) N$_3$, and
  (9) —C(R$^3$)(R$^4$)—OH;

R$^3$ and R$^4$, are each independently selected from the group consisting of
(a) hydrogen,
(b) methyl or ethyl, R$^5$ and R$^{5'}$ are each hydrogen.

Within this sub-class are the compounds of Formula Ia wherein:

R$^1$ is selected from the group consisting of
(a) S(O)$_2$CH$_3$,
(b) S(O)$_2$NH$_2$,
(c) S(O)NHCH$_3$, and
(d) S(O)NHNH$_2$;

R$^2$ is selected from the group consisting of mono or di-substituted phenyl wherein the substituents are selected from the group consisting of
  (1) hydrogen,
  (2) halo, selected from the group consisting of fluoro, chloro and bromo,
  (3) C$_{1-3}$alkoxy,
  (4) C$_{1-3}$alkylthio,
  (5) CN, and
  (6) C$_{1-3}$alkyl;

Within this group are the compounds of Formula Ia wherein R$^2$ is mono or di-substituted phenyl wherein the substituents are selected from the group consisting of
  (1) hydrogen,
  (2) halo, selected from the group consisting of fluoro, chloro and bromo,
  (3) methoxy, and
  (4) methyl.

These compounds may be more particularly defined as the compounds of Formula Ia wherein R$^1$ is selected from the group consisting of
(a) S(O)$_2$CH$_3$, and
(b) S(O)$_2$NH$_2$, R$^2$ is mono or di-substituted phenyl wherein the substituents are selected from the group consisting of
  (1) hydrogen, (2) halo, selected from the group consisting of fluoro, chloro and bromo.

For purposes of this specification mono- or di-substituted heteroaryl of definition $R^2$ is defined as a mono- or di-substituted heteroaryl selected from the group consisting of
(1) 2-furanyl,
(2) 3-furanyl,
(3) 2-thienyl,
(4) 3-thienyl,
(5) 3-isoxazolyl,
(6) 4-isoxazolyl,
(7) 5-isoxazolyl,
(8) 3-isothiazolyl,
(9) 4-isothiazolyl,
(10) 5-isothiazolyl,
(11) 2-oxazolyl,
(12) 4-oxazolyl,
(13) 5-oxazolyl,
(14) 2-thiazolyl,
(15) 4-thiazolyl,
(16) 5-thiazolyl,
(17) 1,2,3-thiadiazol-4-yl,
(18) 1,2,3-thiadiazol-5-yl,
(19) 1,2,4-thiadiazol-3-yl,
(20) 1,2,4-thiadiazol-5-yl,
(21) 1,3,4-thiadiazol-2-yl,
(22) 1,2,5-thiadiazol-3-yl,
(23) 1,2,3-oxadiazol-4-yl,
(24) 1,2,3-oxadiazol-5-yl,
(25) 1,2,4-oxadiazol-3-yl,
(26) 1,2,4-oxadiazol-5-yl,
(27) 1,3,4-oxadiazol-2-yl,
(28) 1,2,5-oxadiazol-3-yl,
(29) pyrazol-4-yl,
(30) pyrazol-4-yl,
(31) pyrazol-5-yl,
(32) 1,2,3-triadiazol-4-yl,
(33) 1,2,3-triadiazol-5-yl,
(34) 1,2,4-triadiazol-3-yl,
(35) 1,2,4-triadiazol-5-yl,
(36) 1,2-diazinyl,
(37) 1,3-diazinyl,
(38) 1,4-diazinyl,
(39) 1,2,3,4-tetrazin-5-yl,
(40) 1,2,4,5-tetrazin-4-yl,
(41) 1,3,4, 5-tetrazin-2-yl, and
(42) 1,2,3,5-tetrazin-4-yl,
wherein the substituents are defined in any definition of $R^2$.

Within the mono- or di-substituted heteroaryl of $R^2$ is the group wherein the substituents are selected from the group consisting of
(a) hydrogen,
(b) fluoro or chloro,
(c) $C_{1-3}$alkoxy,
(d) $C_{1-6}$alkylthio,
(e) CN,
(5) $CF_3$,
(6) $C_{1-3}$alkyl,
(7) —C($R^3$)($R^4$)—OH;
(8) —C($R^3$)($R^4$)—O—$C_{1-4}$alkyl.

Within the mono- or di-substituted heteroaryl of $R_2$ immediately above, is the group wherein the heterocycles are selected from
(1) 3-isoxazolyl,
(2) 4-isoxazolyl,
(3) 5-isoxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,
(21) 1,2,4-oxadiazol-3-yl,
(22) 1,2,4-oxadiazol-5-yl,
(23) 1,3,4-oxadiazol-2-yl,
(24) 1,2,5-oxadiazol-3-yl,
(25) 1,2-diazinyl,
(26) 1,3-diazinyl, and
(27) 1,4-diazinyl.

Within the mono- or all-substituted heteroaryl of $R^2$ immediately above, is the group wherein the heterocycles are selected from
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl,
(9) 5-thiazolyl,
(10) 1,2-diazinyl,
(11) 1,3-diazinyl, and
(12) 1,4-diazinyl, and
wherein the substitutents are selected from the group consisting of
(1) hydrogen,
(2) fluoro or chloro,
(3) $C_{1-3}$alkoxy,
(4) $C_{1-3}$alkylthio,
(5) CN,
(6) $C_{1-3}$alkyl, and
(7) —C($R^3$)($R^4$)—OH,
wherein $R^3$ and $R^4$ are each independently hydrogen, methyl or ethyl.

For purposes of this specification alkyl is defined to include linear, branched, and cyclic structures, with $C_{1-6}$alkyl including including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Exemplifying the invention are:
(a) 3-(4-Fluorophenyl)-4-(4-(methylsulfonyl)phenyl)-2-(5H)-furanone,
(b) 3-(4-Fluorophenyl)-4-(4-(aminosulfonyl)phenyl)-2-(5H)-furanone,
(c) 5,5-Dimethyl-3-(4-fluorophenyl)-4-(4-(methylsulfonyl)phenyl)-2-(5H)-furanone,
(d) 3-(3-Fluorophenyl)-4-(4-(methylsulfonyl)phenyl)-2-(5H)-furanone,
(e) 5,5-Dimethyl-3-(3-fluorophenyl)-4-(4-(methylsulfonyl)phenyl)-2-(5H)-furanone,
(f) 5,5-Dimethyl-3-(3-chlorophenyl)-4-(4-(methylsulfonyl)phenyl)-2-(5H)-furanone,
(g) 3-(3,4-Difluorophenyl)-4-(4-(methylsulfonyl)phenyl)-2-(5H)-furanone,
(h) 3-(3,4-Dichlorophenyl)-4-(4-(methylsulfonyl)phenyl)-2-(5H)-furanone,
(i) 5,5-Dimethyl-3-(3,4-difluorophenyl)-4-(4-(methylsulfonyl)phenyl)-2-(5H)-furanone,
(j) 5,5-Dimethyl-3-(3,4-dichlorophenyl)-4-(4-(methylsulfonyl)phenyl)-2-(5H)-furanone,
(k) 5,5-Dimethyl-3-(4-chlorophenyl)-4-(4-(methylsulfonyl)phenyl)-2-(5H)-furanone,
(l) 3-(2-Naphyhyl)-4-(4-(methylsulfonyl)phenyl)-2-(5H)-furanone,
(m) 5,5-Dimethyl-3-(2-naphyhyl)-4-(4-(methylsulfonyl)phenyl)-2-(5H)-furanone,
(m) 3-phenyl-4-(4-(methylsulfonyl)phenyl)-2-(5H)-furanone.

Further illustrating the invention are
3-(3,4-Difluorophenyl)-4-(4-(methylsulfonyl)phenyl)-2-(5H)-furanone, and
3-phenyl-4-(4-(methylsulfonyl)phenyl)-2-(5H)-furanone,
or a pharmaceutically acceptable salt thereof.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for treatment of osteoporosis.

Within this embodiment the invention encompasses pharmaceutical compositions for treatment of osteoporosis comprising a pharmaceutically acceptable carrier and a non-toxic therapeutically effective amount of compound of Formula I as described above.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenedime, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

As indicated above, pharmaceutical compositions for treating osteoporosis as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain s sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 100 mg/kg of body weight per day are useful in the treatment of the above-indicated conditions, or alternatively about 0.5 mg to about 6 g per patient per day. For example, osteoporosis may be effectively treated by the administration of from about 0.01 to 50 mg of the compound per kilogram of body weight per day, or alternatively about 0.5 mg to about 3.5 g per patient per day, preferably 2.5 mg to 1 g per patient per day. A dosage 1.0 to 100 mg/kg per day or 1.0 to 20 mg/kg per day may prove especially useful.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be Understood, however, that the specific dose level for any particular patient will depend upon a variety of factors including the age body weight, general health, sex, diet, time of administration, route of administration, rate of excretion, drug combination and the severity of the particular disease undergoing therapy.

Methods of Synthesis

The compounds of the present invention can be prepared according to the following methods.

Method A:

An appropriately substituted aryl bromomethyl ketone II is reacted with an appropriately substituted aryl acetic acid III in a solvent such as acetonitrile in the presence of a base such as triethylamine and then treated with 1,8-diazabicyclo [5.4.0]undec-7-ene (DBU) to afford the lactone IV. Isomeric lactone VII is prepared by reacting phenylacetic acid V with bromoketone VI under similar conditions.

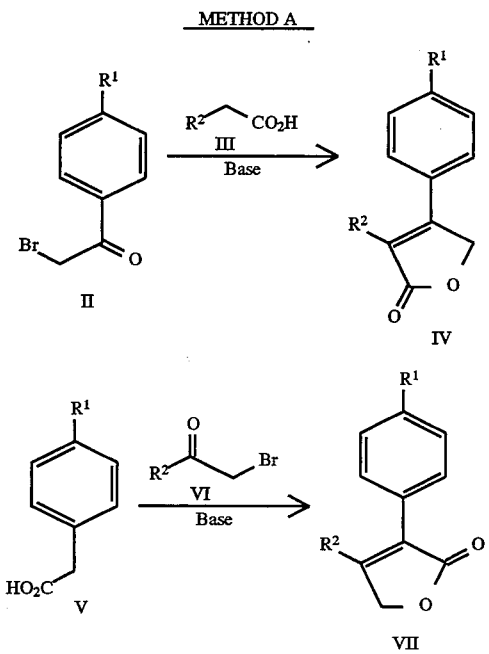

( $R^2$ is a mono- or disubstituted phenyl or a mono- or disubstituted heteroaryl )

Method B:

Methyl 2-hydroxy isobutyrate VIII is silylated with TMSCl to give the TMS ether IX, which is treated with the organomatallic X to provide ketone XI. Desilylation followed by acylation yields keto-ester XIV, which can be cyclized to lactone XV by base catalysis. Oxidation of XV with MMPP or mCPBA affords the desired product XVI.

METHOD B

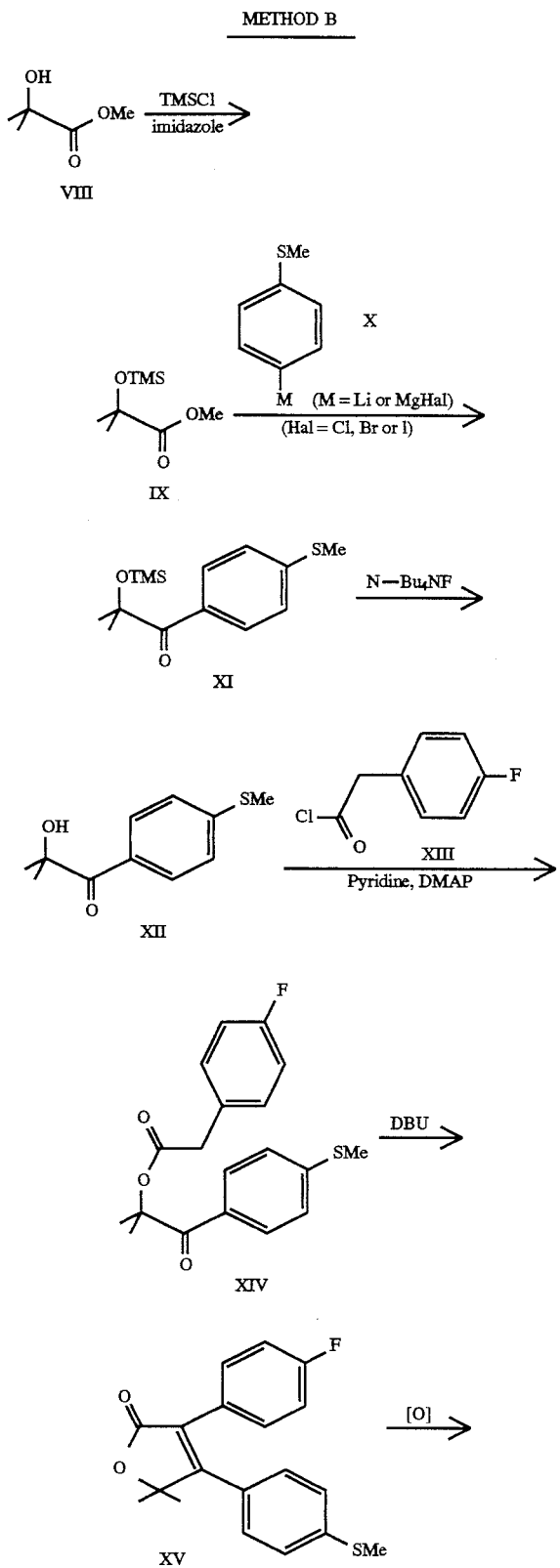

-continued
METHOD B

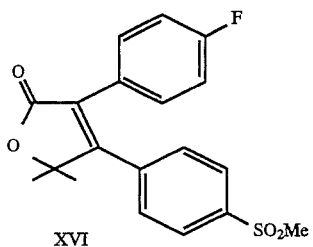

METHOD C

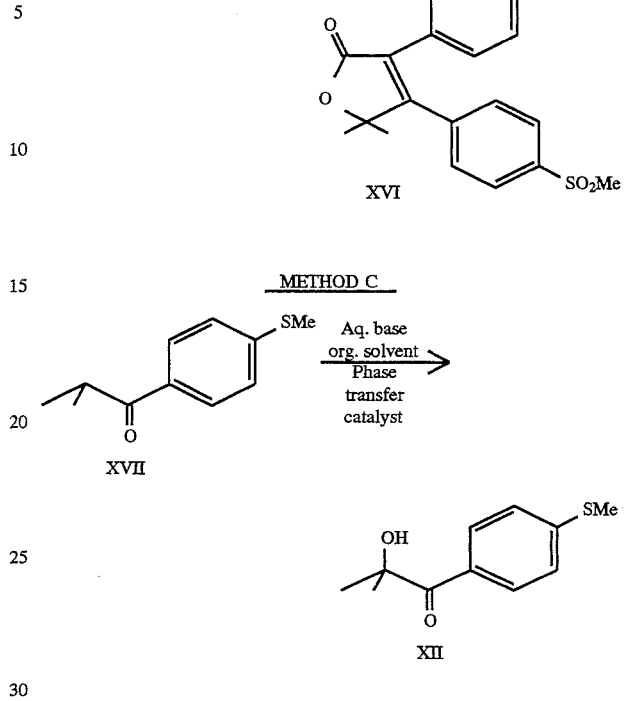

An alternative preparation of the hydroxy ketone XII is the oxidation of the known (*J. Org. Chem.* 1991 56, 5955–8; *Sulfur Lett.* 1991, 12, 123–32) ketone XVII. A mixture of XVII, aqueous base, such as NaOH, organic solvents such as carbon tetrachloride/-toluene and a phase transfer catalyst such as ALIQUAT 336 is stirred in air at room temperature to provide XII. Compound XII is also described in U.S. Pat. No. 4,321,118 and *Org. Coat.* 1986, 6, 175–95.

METHOD D

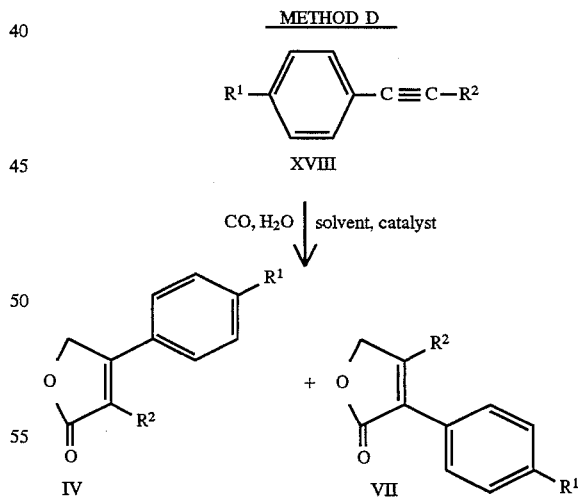

By reacting an acetylene XVIII with carbon monoxide and water in the presence of suitable catalysts, a mixture of compound IV and its isomer VII is obtained. The isomers are separable by standard procedures in the art such as chromatography or crystallization. Examples of useful catalysts and conditions are $PdCl_2$ in aqueous HCl and EtOH, heated at 50°–150° C. and 50–150 atmospheres of pressure, or $Rh_4(CO)_{12}$ (or $Rh_6(CO)_{16}$) in aqueous THF (or acetone, acetonitrile, benzene, toluene, EtOH, MeOH) containing a trialkylamine, at 50°–150° C. and 20–300 atmospheres pressure. See Takahashi et al., *Organometallics* 1991, 10, 2493–2498; and Tsuji et al., *J. Am. Chem. Soc.* 1966, 88, 1289–1292.

oxidized to a sulfone by various oxidizing agents such as peracetic acid, MPPM, MMPP or $H_2O_2$ to give the desired compound XXV. See Y. Ito et al., *J. Am. Chem. Soc.* 1979,101, 494, footnote 2; and P. Magnus et al., *Tet. Lett.* 1992, 2933.

Representative Compounds

Tables I and II illustrate compounds of Formula I.

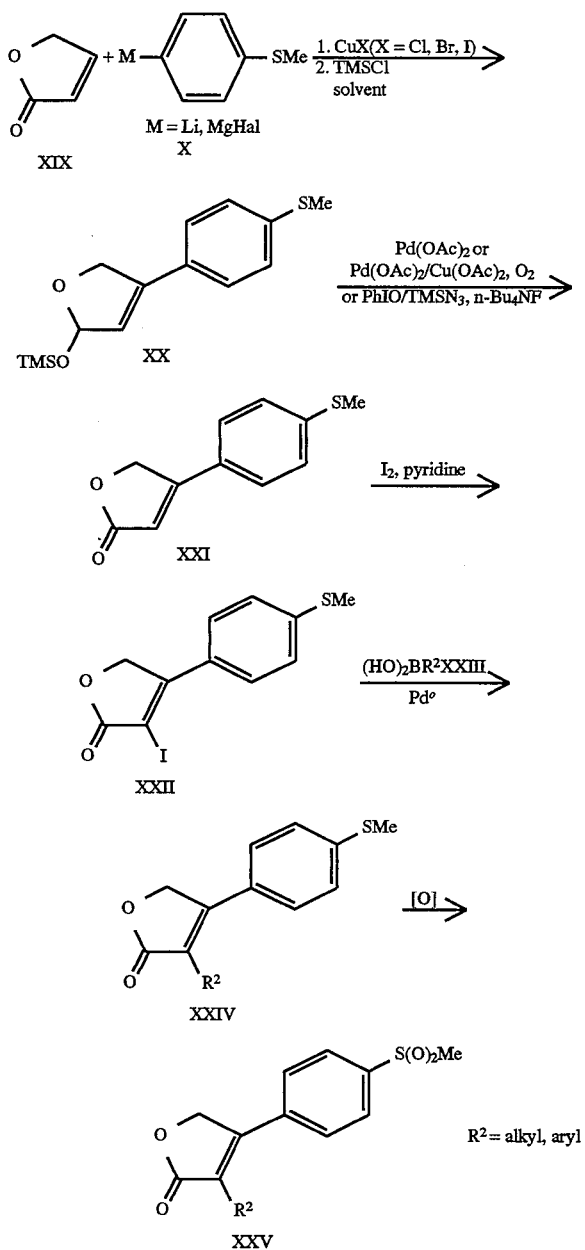

1,4-Addition to XIX of 4-methylthiophenyl organometallic reagents X in the presence of copper salts and the trapping of the resultant enolate with trialkyl silyl chloride such as TMSCl or TIPSCl provide the ketene acetal XX. The ketene acetal can then be oxidized to the substituted butenolide XXI by the method of Ito using $Pd(OAc)_2$ or catalytic amounts of $Pd(OAc)_2$ and $Cu(OAc)_2$ with $O_2$ in MeOH or by the method of Magnus using $PhIO/TMSN_3$ and $Bu_4NF$. Introduction of the iodine can be accomplished by treating XXI with $I_2$ in the presence of pyridine to afford XXII. Palladium catalyzed Suzuki or Stille coupling of XXIII with the appropriate aryl or alkyl partner such as the boronic acid XXIII provides the butenolide XXIV. The sulfide can be TABLE I-continued

| Example | Structure | Method |
|---|---|---|
| 6 | 2,6-difluorophenyl furanone with 4-(SO₂Me)phenyl | A |
| 7 | 2,5-difluorophenyl furanone with 4-(SO₂Me)phenyl | A |
| 8 | 3,5-difluorophenyl furanone with 4-(SO₂Me)phenyl | A |
| 9 | 4-bromophenyl furanone with 4-(SO₂Me)phenyl | A |
| 10 | 4-chlorophenyl furanone with 4-(SO₂Me)phenyl | A |
| 11 | 4-methoxyphenyl furanone with 4-(SO₂Me)phenyl | A |
| 12 | phenyl furanone with 4-(SO₂Me)phenyl | A |
| 13 | 2-chlorophenyl furanone with 4-(SO₂Me)phenyl | A |
| 14 | 2-bromo-4-fluorophenyl furanone with 4-(SO₂Me)phenyl | A |
| 15 | 2-bromo-4-chlorophenyl furanone with 4-(SO₂Me)phenyl | A |
| 16 | 2-fluoro-4-chlorophenyl furanone with 4-(SO₂Me)phenyl | A |
| 17 | 3-bromo-4-fluorophenyl furanone with 4-(SO₂Me)phenyl | A |

TABLE I-continued

| Structure | Example | Method |
|---|---|---|
| 3-Cl-C6H4 / 4-SO2Me-C6H4 furanone | 18 | A |
| 2-Cl,4-F-C6H3 / 4-SO2Me-C6H4 furanone | 19 | A |
| 2,4-Cl2-C6H3 / 4-SO2Me-C6H4 furanone | 20 | A |
| 3,4-Cl2-C6H3 / 4-SO2Me-C6H4 furanone | 21 | A |
| 2,6-Cl2-C6H3 / 4-SO2Me-C6H4 furanone | 22 | A |
| 4-F,3-Cl-C6H3 / 4-SO2Me-C6H4 furanone | 23 | A |
| 4-CF3-C6H4 / 4-SO2Me-C6H4 furanone | 24 | A |
| 4-OMe,3-F-C6H3 / 4-SO2Me-C6H4 furanone | 25 | A |
| 4-OMe,3-Cl-C6H3 / 4-SO2Me-C6H4 furanone | 26 | A |
| 4-OMe,3-Br-C6H3 / 4-SO2Me-C6H4 furanone | 27 | A |
| 2-F-C6H4 / 4-SO2Me-C6H4 furanone | 28 | A |
| 4-SMe-C6H4 / 4-SO2Me-C6H4 furanone | 29 | A |

TABLE I-continued

| Structure | Example | Method |
|---|---|---|
| 3-(3-fluorophenyl)-4-(4-methylsulfonylphenyl) furanone | 30 | A |
| 3-(2-chloro-6-fluorophenyl)-4-(4-methylsulfonylphenyl) furanone | 31 | A |
| 3-(3-bromo-4-methylphenyl)-4-(4-methylsulfonylphenyl) furanone | 32 | A |
| 3-(4-bromo-2-fluorophenyl)-4-(4-methylsulfonylphenyl) furanone | 33 | A |
| 3-(3,4-dibromophenyl)-4-(4-methylsulfonylphenyl) furanone | 34 | A |
| 3-(4-chloro-3-fluorophenyl)-4-(4-methylsulfonylphenyl) furanone | 35 | A |
| 3-(4-bromo-3-fluorophenyl)-4-(4-methylsulfonylphenyl) furanone | 36 | A |
| 3-(4-bromo-2-chlorophenyl)-4-(4-methylsulfonylphenyl) furanone | 37 | A |
| 3-(2-naphthyl)-4-(4-methylsulfonylphenyl) furanone | 38 | A |
| 3-(7-quinolinyl)-4-(4-methylsulfonylphenyl) furanone | 39 | A |
| 3-(3,4-dichlorophenyl)-4-(4-sulfamoylphenyl) furanone | 40 | A |
| 3-(3,4-difluorophenyl)-4-(4-sulfamoylphenyl) furanone | 41 | A |

TABLE I-continued

| | Example | Method |
|---|---|---|
| (structure: 4-OMe, 3-Cl phenyl / 4-SO₂NH₂ phenyl furanone) | 42 | A |
| (structure: 4-OMe, 3-Br phenyl / 4-SO₂NH₂ phenyl furanone) | 43 | A |
| (structure: 4-SO₂Me phenyl / 3-Cl phenyl dimethyl furanone) | 44 | B + C |
| (structure: 4-SO₂Me phenyl / 2-naphthyl dimethyl furanone) | 45 | B + C |
| (structure: 4-SO₂Me phenyl / 3,4-diF phenyl dimethyl furanone) | 46 | B + C |
| (structure: 4-SO₂Me phenyl / 3,4-diCl phenyl dimethyl furanone) | 47 | B + C |
| (structure: 4-SO₂Me phenyl / 4-Cl phenyl dimethyl furanone) | 48 | B + C |

TABLE II

| (structure: 4-F phenyl / 4-SO₂NH₂ phenyl furanone) |
| (structure: 4-SO₂NH₂ phenyl / 2,4-diF phenyl furanone) |
| (structure: 4-SO₂NH₂ phenyl / 4-Cl phenyl furanone) |
| (structure: 4-SO₂NH₂ phenyl / 4-F phenyl dimethyl furanone) |
| (structure: 4-F phenyl / 4-SO₂NH₂ phenyl dimethyl furanone) |

TABLE II-continued
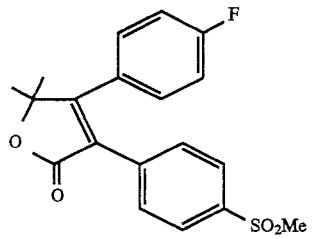
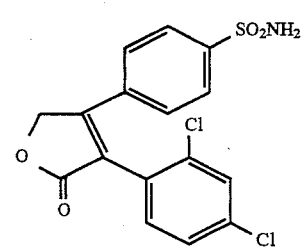
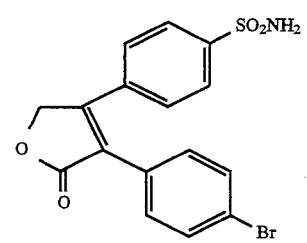
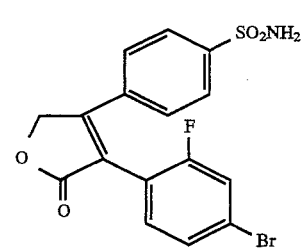
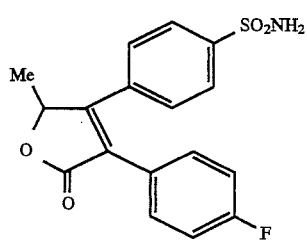
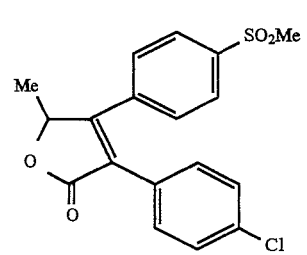
TABLE II-continued
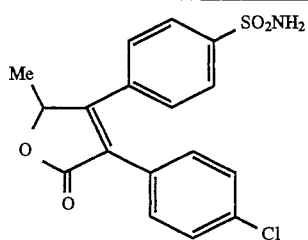
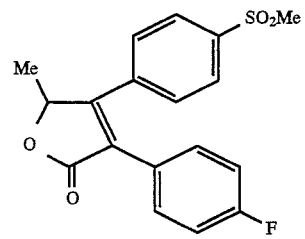
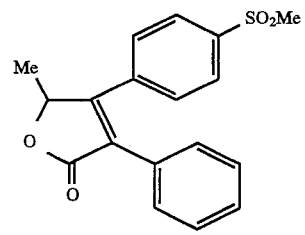
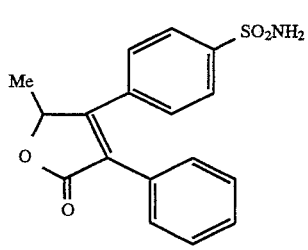
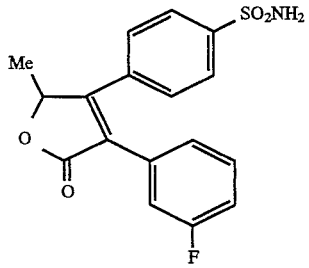
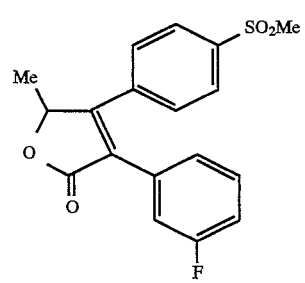

TABLE II-continued

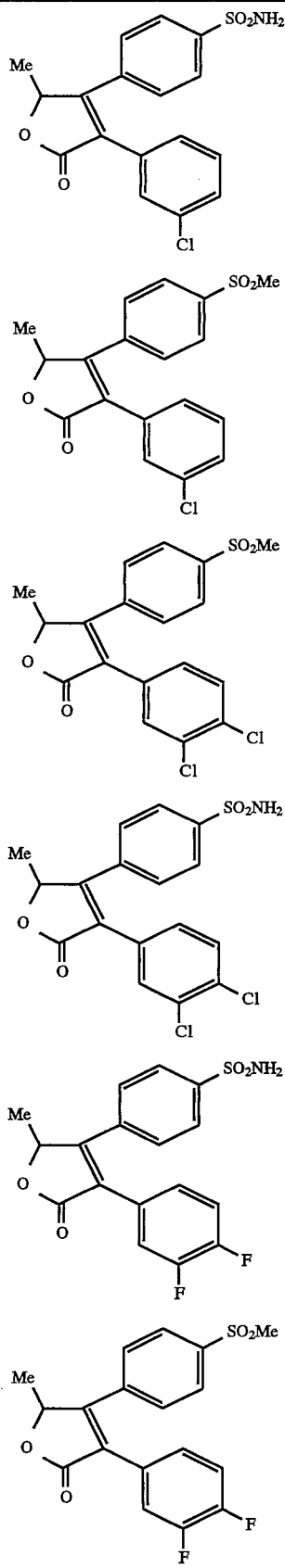
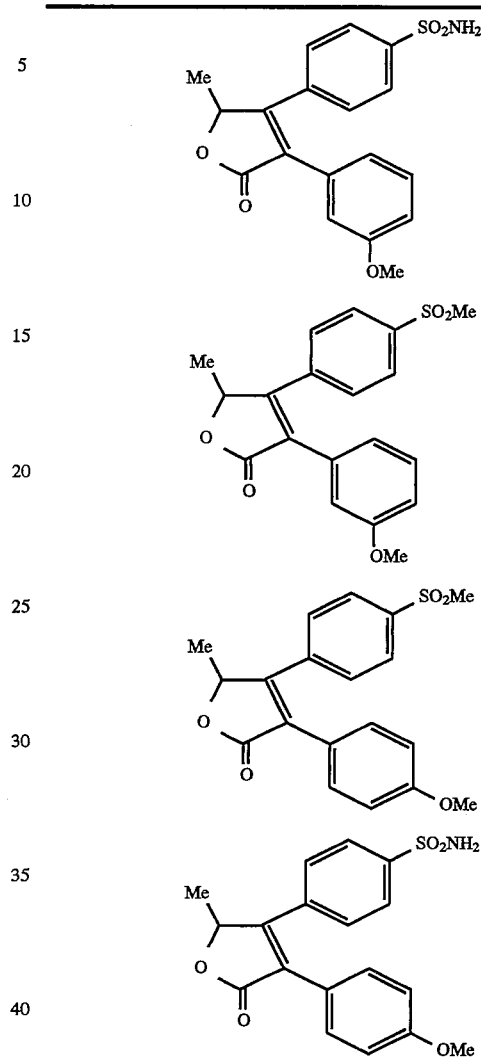

The compounds of the invention will now be illustrated by the following non-limiting examples in which, unless stated otherwise:

(i) all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m.

multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=acetyl
Bn=benzyl
DBU=1,8-diazabicyclo[5.4.0]undec-7-ene
DIBAL=diisobutylaluminum hydride
DMAP=4-(dimethylamino)pyridine
DMF=N,N-dimethylformamide
Et$_3$N=triethylamine
LDA=lithium diisopropylamide
m-CPBA=metachloroperbenzoic acid
MMPP=monoperoxyphtalic acid
MPPM=monoperoxyphthalic acid, magnesium salt 6H$_2$O
Ms=methanesulfonyl=mesyl=SO$_2$Me
MsO=methanesulfonate=mesylate
NSAID=non-steroidal anti-inflammatory drug
OXONE®=2KHSO$_5$•KHSO$_4$•K$_2$SO$_4$
PCC=pyridinium chlorochromate
PDC=pyridinium dichromate
Ph=phenyl
Phe=benzenediyl
Pye=pyridinediyl
r.t=room temperature
rac.=racemic
SAM=aminosulfonyl or sulfonamide or SO$_2$NH$_2$
TBAF=tetra-n-butylammonium fluoride
Th=2- or 3-thienyl
TFAA=trifluoroacetic acid anhydride
THF=tetrahydrofuran
Thi=thiophenediyl
TLC=thin layer chromatography
TMS-CN trimethylsilyl cyanide
Tz=1H (or 2H)-tetrazol-5-yl
C$_3$H$_5$=allyl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

EXAMPLE 1

3-(4-Fluorophenyl)-4-(4-(methylsulfonyl)phenyl)-2-(5H)-furanone

Step 1: 2-Bromo-1-(4-(methylsulfonyl)phenyl)ethanone

A solution of 197 g of 4-(methylthio)acetophenone (ref: JACS, 1952, 74, p. 5475) in 700 mL of MeOH and 3500 mL of CH$_2$Cl$_2$ was added 881 g of MMPP over a period of 30 min. After 3 h at room temperature the reaction mixture was filtered and the filtrate was washed with 2 L of saturated aqueous solution of NaHCO$_3$ and 1 L of brine. The aqueous phase was further extracted with 2 L of CH$_2$Cl$_2$. The combined extracts was dried over Na$_2$SO$_4$ concentrated to give 240 g of 4-(methylsulfonyl)acetophenone as a white solid.

To a cooled (−5° C.) solution of 174 g of 4-(methylsulfonyl)acetophenone in 2.5 L of CHCl$_3$ was added 20 mg of AlCl$_3$, followed by a solution of 40 mL of Br$_2$ in 300 mL CHCl$_3$. The reaction mixture was then treated with 1.5 L of water and the CHCl$_3$ was separated. The aqueous layer was extracted with 1 L of EtOAc. The combined extracts was dried over Na$_2$SO$_4$ and concentrated. The crude product was recystalized from 50/50 EtOAc/hexane to give 210 g of the title compound as a white solid.

Step 2:

To the product of Step 1 (216 mg) dissolved in acetonitrile (4 mL) was added Et$_3$N (0.26 mL), followed by 4-fluorophenylacetic acid (102 mg). After 1.5 h at room temperature 0.23 mL of DBU was added. The reaction mixture was stirred for another 45 min and then treated with 5 mL of 1N HCl. The product was extracted with EtOAc, dried over Na$_2$SO$_4$ and concentrated. The residue was purified by flash chromatography (40% EtOAc in hexane) to yield 150 mg of the title compound as a solid.

$^1$H NMR (CD$_3$COCD$_3$) δ 3.15 (3H, s), 5.36 (3H, s), 7.18 (2H, J=8.9 Hz, t), 7.46 (2H, m), 7.7 (2H, J=8.65 Hz, d), 7.97 (2H, J=8.68, d).

EXAMPLE 2

3-(4-Fluorophenyl)-4-(4-(aminosulfonyl)phenyl)-2-(2H)-furanone $^1$H NMR (CD$_3$COCD$_3$) δ 5.34 (2H, s), 6.67 (2H, bd), 7.18 (2H, m), 7.46 (2H, m), 7.61 (2H, m), 7.90 (2H, m).

M.P. 187°–188° C. (d).

EXAMPLE 3

5,5-Dimethyl-3-(4-fluorophenyl)-4-(4-(methylsulfonyl)phenyl)-2-(5H)-furanone

Step 1: Methyl 2-trimethylsilyloxyisobutyrate

To a solution of 1.2 mL (10.4 mmol) of methyl 2-hydroxyisobutyrate in 50 mL of CH$_2$Cl$_2$ were added 1.2 g (17.6 mmol) of imidazole and 2.1 mL (16.6 mmol) of TMSCl. The mixture was stirred at r.t. for 1.5 h and quenched with 20 mL of H$_2$O. The organic layer was dried over MgSO$_4$, concentrated and passed through a short plug of silica gel eluted with 9:1 hexane/EtOAc. Evaporation of solvent afforded 1.27 g of the title compound as a colorless oil.

$^1$H NMR (CD$_3$COCD$_3$) δ0.08 (9H, s), 1.38 (6H, s), 3.67 (3H, s).

Step 2: 2-Trimethylsilyloxy-4'-(methylthio) isobutyrophenone

A solution of 204 mg (1.0 mmol) of 4-bromothioanisole in 2.5 mL of THF was cooled to −78° C. and treated with 0.42 mL of 2.5M n-BuLi solution in hexane. After stirring at −78° C. for 1 h, a solution of 380 mg (2.0 mmol) of methyl 2-trimethylsilyloxyisobutyrate in 2 mL of THF was added. The mixture was stirred at −78° C. for 2 h and then quenched with NH$_4$OAc buffer. The product was extracted with EtOAc, dried over MgSO$_4$ and concentrated. The residue was purified by flash chromatography, eluting with 19:1 hexane/EtOAc to give 95 mg of the title product.

$^1$H NMR (CD$_3$COCD$_3$) δ0.05 (9H, s), 1.52 (6H, s), 2.53 (3H, s), 7.33 (2H, d), 8.12 (2H, d).

Step 3: 2-Hydroxy-4'-(methylthio)isobutyrophenone

To a solution of 40 mg (0.14 mmol) of 2-trimethylsilyloxy-4'-(methylthio)isobutyrophenone in 2 mL THF was added 0.2 mL of 1M n-Bu$_4$NF in THF. The resulting mixture was stirred for 30 min and then quenched with 10 mL of NH$_4$OAc buffer. The product was extracted with EtOAc, dried over MgSO$_4$ and concentrated. The residue was purified by flash chromatography, eluting with 4:1 hexane/EtOAc to give 25 mg of the title product.

$^1$H NMR (CD$_3$COCD$_3$) δ 1.50 (6H, s), 2.54 (3H, s), 4.68 (1H, s), 7.30 (2H, d), 8.15 (2H, d).

Step 4: 2-(4-Fluorophenylacetoxy)-4'-(methylthio) isobutyrophenone

To a solution of 72 mg (0.34 mmol) 2-hydroxy-4'-(methylthio)isobutyrophenone in 1.7 mL of CH$_2$Cl$_2$ were added 0.2 mL of pyridine and 140 mg (0.81 mmol) of 4-fluorophenylacetyl chloride. The mixture was stirred at r.t. overnight and then quenched with NH$_4$OAc buffer. The product was extracted with EtOAc, dried over MgSO$_4$ and concentrated. The crude product was purified by flash chromatography eluting with 8:1 hexane/EtOAc to give 95 mg of the title product.

$^1$H NMR (CD$_3$COCD$_3$) δ 1.62 (3H, s), 1.67 (3H, s), 2.48 (3H, s), 3.79 (2H, s), 7.0–7.3 (6H, m), 7.78 (2H, d).

Step 5: 5,5-Dimethyl-3-(4-fluorophenyl-4-(4-(methylthio) phenyl)-2-(5H)-furanone To a solution of 95 mg of 2-(4-fluorophenylacetoxy)-4'-(methylthio)isobutyrophenone in 4 mL of CH$_2$Cl$_2$ was added 0.2 mL of DBU. The mixture was stirred for 4 h and diluted with NH$_4$OAc buffer. The product was extracted with EtOAc, dried over MgSO$_4$ and concentrated. The residue was purified by flash chromatography, eluting with 20:1 toluene/EtOAc to give 75 mg of the title product.

$^1$H NMR (CD$_3$COCD$_3$) δ 1.58 (6H, s), 2.50 (3H, s), 7.03 (2H, dd), 7.25–7.35 (4H, m), 7.41 (2H, dd).

Step 6: 5,5-Dimethyl-3-(4-fluorophenyl)-4-(4-(methylsulfonyl)phenyl)-2-(5H)-furanone To a solution of 81 mg of 5,5-dimethyl-3-(4-fluorophenyl)-4-(4-(methylthio)phenyl)-2-(5H)-furanone in 1.8 mL of CH$_2$Cl$_2$ and 0.2 mL of MeOH was added 250 mg of MPPM. The reaction mixture was stirred at room temperature for 1 h and then quenched with aqueous NaHCO$_3$. The product was extracted with EtOAc, dried over MgSO$_4$ and concentrated. The crude product was purified by flash chromatography eluting with 1:1 hexane/EtOAc to give 73 mg of the title product.

$^1$H NMR (CD$_3$COCD$_3$) δ 1.62 (6H, s), 3.15 (3H, s), 7.02 (2H, dd), 7.40 (2H, dd), 7.65 (2H, d), 8.03 (2H, d).

EXAMPLE 4

3-(2,4-Difluorophenyl)-4-(4-(methylsulfonyl) phenyl)-2-(5H)-furanone

Analysis calculated for C$_{17}$H$_{12}$F$_2$O$_4$S C, 58.28; H, 3.45; S, 9.15 Found: C, 58.27; H, 3.50; S, 9.27

EXAMPLE 5

3-3,4-Difluorophenyl)-4-(4-methylsulfonyl)phenyl-2-(5H)-furanone

To a solution of 3,4-difluorophenylacetic acid (ALDRICH CHEMICAL) (10 g) and 2-bromo-1-(4-(methylsulfonyl) phenyl)ethanone (Example 9, Step 1) (17.3 g) in acetonitrile (200 mL) at room temperature was added slowly Et$_3$N (20.2 mL). After 1 h at r.t., the mixture was cooled in an ice bath and treated with 17.4 mL of DBU. After 2 h at 0° C., the mixture was treated with 200 mL of 1N HCl and the product was extracted with EtOAc, dried over Na$_2$SO$_4$ and concentrated. The residue was applied on top of a silica gel plug (sintered glass funnel) eluted with 75% EtOAc/hexane, giving, after evaporation of the solvent and swishing in EtOAC, 10 g of the title compound.

Analysis calculated for C$_{17}$H$_{12}$F$_2$O$_4$S C, 58.28; H, 3.45; S, 9.15 Found: C, 58.02; H, 3.51; S, 9.35

EXAMPLE 6

3-(2,6-Difluorophenyl)-4-(4-(methylsulfonyl) phenyl)-2-(5H)-furanone

Analysis calculated for C$_{17}$H$_{12}$F$_2$O$_4$S C, 58.28; H, 3.45; S, 9.15 Found: C, 58.18; H, 3.50; S, 9.44

EXAMPLE 7

3-(2,5-Difluorophenyl)-4-(4-(methylsulfonyl) phenyl)-2-(5H)-furanone

Analysis calculated for C$_{17}$H$_{12}$F$_2$O$_4$S C, 58.28; H, 3.45; S, 9.15 Found: C, 58.89; H, 3.51; S, 9.11

EXAMPLE 8

3-(3,5-Difluorophenyl)-4-(4-(methylsulfonyl) phenyl)-2-(5H)-furanone

Analysis calculated for C$_{17}$H$_{12}$F$_2$O$_4$S C, 58.28; H, 3.45; S, 9.15 Found: C, 58.27; H, 3.62; S, 9.32

EXAMPLE 9

3-(4-Bromophenyl)-4-(4-(methylsulfonyl)phenyl)-2-(5H)-furanone

Analysis calculated for C$_{17}$H$_{13}$BrO$_4$S C, 51.94; H, 3.33; S, 8.16 Found: C, 51.76; H, 3.42; S, 8.21

EXAMPLE 10

3-(4-Chlorophenyl)-4-(4-(methylsulfonyl)phenyl)-2-(5H)-furanone $^1$H NMR (300 MHz, CDCl$_3$) δ 7.93 (2H, d), 7.49 (2H, d), 7.35 (4H, m), 5.16 (2H, s), 3.06 (3H, s)

EXAMPLE 11

3-(4-Methoxyphenyl)-4-(4-(methylsulfonyl)phenyl)-2-(5H)-furanone

Analysis calculated for C$_{18}$H$_{16}$O$_5$ S C, 62.78 H, 4.68; S, 9.31 Found: C, 62.75; H, 4.72; S, 9.39

EXAMPLE 12

3-(Phenyl)-4-(4-(methylsulfonyl)phenyl)-2-(5H)-furanone

To a solution of phenylacetic acid (27.4 g, 201 mmol) and 2-bromo-1-(4-(methylsulfonyl)phenyl)ethanone (Example 1, Step 1)(60 g, 216 mmol, 1.075 eq.) in acetonitrile (630 mL) at 25° C. was added slowly Et$_3$N (30.8 mL, 1.1 eq.). The mixture was stirred for 20 min. at room temperature and then cooled in an ice bath. DBU (60.1 mL, 3 eq.) was slowly added. After stirring for 20 min. in the ice bath, the reaction was complete and the mixture was acidified with 1N HCl (color changes from dark brown to yellow). Then 2.4 L of ice and H$_2$O were added, stirred for a few minutes, then the precipitate was filtered and rinsed with H$_2$O (giving 64 g of crude wet product). The solid was dissolved in 750 mL of CH$_2$Cl$_2$ (dried over MgSO$_4$, filtered) and 300 g of silica gel was added. The solvent was evaporated to near dryness (silica gel a bit sticky) and the residue was applied on top of a silica gel plug (sintered glass funnel), eluted with 10%

EtOAc/CH$_2$Cl$_2$, giving, after evaporation of the solvent and swishing in EtOAC, 36.6 g (58%) of the title compound.

Analysis calculated for C$_{17}$H$_{14}$O$_4$S C, 64.95; H, 4.49; S, 10.20 Found: C, 64.63; H, 4.65; S, 10.44

EXAMPLE 12A 3-(Phenyl)-4-(4-(methylsulfonyl)phenyl)-2-(5H)-furanone

Into a 20 mL glass ampule are added 1 g of 2-(4-(methylsulfonyl)phenyl)phenylacetylene, 20 mg of Rh$_4$(CO)$_{12}$, 1.5 g of Et$_3$N, 10 mL of THF, 1 mL of H$_2$O under a nitrogen atmosphere, and the ampule is placed in a 100-mL stainless steel autoclave. The reaction system is flushed three times with CO then charged at r.t. to an initial CO pressure of 100 atm. The reaction is carried at 100° C. for 5 h. The solution is then diluted with 50 mL of benzene and washed with brine and 1N HCl. The benzene solution is dried over Na$_2$SO$_4$, and concentrated. The crude products are separated by column chromatography on silica gel, eluting with 2:1 EtOAc/hexane to give the title compound and its regioisomer, 4-(phenyl)-3-(4-(methylsolfonyl)phenyl-2-(5H)-furanone.

EXAMPLE 12B 3-(Phenyl)-4-(4-(methylsulfonyl)phenyl)-2-(5H)-furanone

Step 1: 2-trimethylsilyloxy-4-(4-(methylthio)phenyl)-3,4-dihydrofuran

To a solution of 3.86 g (19 mmol) of 4-bromothioanisole in 90 mL of Et$_2$O cooled at −78° C., is added 22 mL of 1.7M solution of t-BuLi in pentane (38 mmol) dropwise. The reaction mixture is stirred for 15 min at −78° C. and 3.8 g of CuI is added and the reaction mixture is allowed to warm to −40° C. over a period of 30 min. A solution of 1.7 g of 2(5H)-furanone in 10 mL of THF is added. After stirring for 1 h, 2 mL of freshly distilled TMSCl is added dropwise. The reaction mixture is then treated with 2 mL of Et$_3$N and 50 mL of sat. NaHCO$_3$, and extracted with 100 mL of Et$_2$O. The Et$_2$O layer is dried over Na$_2$SO$_4$ and concentrated to give the crude title compound which is used for the next step without further purification.

Step 2: 4-(4-(methylthio)phenyl)-2-(5H)-furanone

To a solution of 4 g of Pd(OAc)$_2$ in 100 mL of acetonitrile is added dropwise the crude product from Step 1 (5 g) under nitrogen at r.t. After 10 h at r.t., the mixture is condensed under reduced pressure and the residue is purified by flash chromatography on silica gel eluted with 2:1 hexane/EtOAc to give the title compound.

Step 3: 3-iodo-4-(4-(methylthio)phenyl)-2-(5H)-furanone

To a solution of 3 g of the product of Step 2 in 30 ml of pyridine is added 8.7 g of I2. The mixture is stirred for 24 h and then diluted with 200 mL of Et$_2$O, washed with 100 mL of 5N HCl and 50 mL of 5N Na$_2$S$_2$O$_3$. The Et$_2$O layer is dried over Na$_2$SO$_4$ and concentrated to give the title compound.

Step 4: 3-(Phenyl)-4-(4-(methylthio)phenyl)-2-(5H)-furanone

A mixture of 4 g of the product of Step 3, 3.7 g of PhB(OH)$_2$, 0.4 g of Ph$_3$As, 0.4 g of PdCl$_2$(PhCN)$_2$ in 100 mL of benzene and 15 mL of 2N NaOH is refluxed for 6 h. Ether (200 mL) is then added and the mixture is washed with 100 mL of saturated NaHCO$_3$. The organic layer is dried over MgSO$_4$ and concentrated. The residue is purified by flash chromatography on silica gel eluted with 4:1 hexane/EtOAc to give the title compound.

Step 5: 3-(Phenyl)-4-(4-(methylsulfonyl)phenyl)-2-(5H)-furanone

To a solution of 3 g of the product of Step 4 in 80 mL of 10:1 CH$_2$Cl$_2$/MeOH is added 5.5 g of MPPM. The reaction mixture is stirred at room temperature for 2 h and then diluted with 100 mL of 1:1 hexane/EtOAc. After filtration and concentration, the residue is purified by flash chromatography eluted with 2:1 EtOAc/hexane to give the title product.

EXAMPLE 13

3-(2-Chlorophenyl)-4-(4-(methylsulfonyl)phenyl)-2-(5H)-furanone

Analysis calculated for C$_{17}$H$_{13}$ClO$_4$S C, 58.54; H, 3.76; S, 9.19 Found: C, 58.59; H, 3.80; S, 9.37

EXAMPLE 14

3-(2-Bromo-4-fluorophenyl)-4-(4-(methylsulfonyl)phenyl)-2-(5H)-furanone

Analysis calculated for C$_{17}$H$_{12}$BrFO$_4$S C, 49.75; H, 2.93 Found: C, 49.75; H, 3.01

EXAMPLE 15

3-(2-Bromo-4-chlorophenyl)-4-(4-(methylsulfonyl)phenyl)-2-(5H)-furanone $^1$H NMR (300 MHz, acetone-d$_6$) δ 7.95 (2H, d), 7.85 (1H, d), 7.63 (2H, dd), 7.55 (1H, dd), 7.45 (1H, d), 5.50 (2H, s), 3.15 (3H, s)

EXAMPLE 16

3-(4-Chloro-2-fluorophenyl)-4-(4-(methylsulfonyl)phenyl)-2-(5H)-furanone $^1$H NMR (300 MHz, acetone-d$_6$) δ 8.0 (2H, d), 7.70 (2H, d), 7.50–7.30 (3H, m), 5.35 (2h, s), 3.15 (3H, s)

EXAMPLE 17

3-(3-Bromo-4-fluorophenyl)-4-(4-(methylsulfonyl)phenyl)-2-(5H)-furanone

Analysis calculated for C$_{17}$H$_{12}$BrFO$_4$S C, 49.75; H, 2.93 Found: C, 49.44; H, 2.98

EXAMPLE 18

3-(3-Chlorophenyl)-4-(4-(methylsulfonyl)phenyl)-2-(5H)-furanone

Analysis calculated for C$_{17}$H$_{13}$ClO$_4$S C, 58.54; H, 3.76 Found: C, 58.29; H, 3.76

EXAMPLE 19

3-(2-Chloro-4-fluorophenyl)-4-(4-(methylsulfonyl)phenyl)-2-(5H)-furanone

Analysis calculated for C$_{17}$H$_{12}$ClFO$_4$S C, 55.67; H, 3.30 Found: C, 55.67; H, 3.26

EXAMPLE 20

3-(2,4-Dichlorophenyl)-4-(4-(methylsulfonyl)phenyl)-2-(5H)-furanone

Analysis calculated for C$_{17}$H$_{12}$Cl$_2$O$_4$S C, 53.28; H, 3.16; S, 8.37 Found: C, 52.89; H, 3.23; S, 8.58

EXAMPLE 21

3-(3,4-Dichlorophenyl)-4-(4-(methylsulfonyl)phenyl)-2-(5H)-furanone

Analysis calculated for $C_{17}H_{12}Cl_2O_4S$ C, 53.28; H, 3.16; S, 8.37 Found: C, 53.07; H, 3.32; S, 8.51

EXAMPLE 22

3-(2,6-Dichlorophenyl)-4-(4-(methylsulfonyl)phenyl)-2-(5H)-furanone

Analysis calculated for $C_{17}H_{12}Cl_2O_4S$ C, 53.28; H, 3.16; S, 8.37 Found: C, 52.99; H, 3.22; S, 8.54

EXAMPLE 23

3-(3-Chloro-4-fluorophenyl)-4-(4-(methylsulfonyl)phenyl)-2-(5H)-furanone $^1$H NMR (300 MHz, acetone-$d_6$) δ 8.0 (2H, d), 7.70 (2H, d), 7.60 (1H, d), 7.25–7.40 (2H, m), 5.35 (2H, s), 3.15 (3H, s)

EXAMPLE 24

3-(4-Trifluoromethylphenyl)-4-(4-(methylsulfonyl)phenyl)-2-(5H)-furanone $^1$H NMR ($CD_3COCD_3$) δ 8.10 (2H, d), 7.82–7.93 (4H, m), 7.75 (2H, d), 5.55 (2H, s), 3.30 (3H, s)

EXAMPLE 25

3-(3-Fluoro-4-methoxyphenyl)-4-(4-(methylsulfonyl)phenyl)-2-(5H)-furanone

Analysis calculated for $C_{18}H_{15}FO_5S$ C, 59.66; H, 4.17 Found: C, 59.92; H, 4.37

EXAMPLE 26

3-(3-Chloro-4-methoxyphenyl)-4-(4-(methylsulfonyl)phenyl)-2-(5H)-furanone

Analysis calculated for $C_{18}H_{15}ClO_5S$ C, 57.07; H, 3.99 Found: C, 57.29; H, 4.15

EXAMPLE 27

3-(3-Bromo-4-methoxyphenyl)-4-(4-(methylsulfonyl)phenyl)-2-(5H)-furanone

Analysis calculated for $C_{18}H_{15}BrO_5S$ C, 51.08; H, 3.57 Found: C, 51.38; H, 3.62

EXAMPLE 28

3-(2-Fluorophenyl)-4-(4-(methylsulfonyl)phenyl)-2-(5H)-furanone

Analysis calculated for $C_{17}H_{13}FO_4S$ C, 61.44; H, 3.94 Found: C, 61.13; H, 3.85

EXAMPLE 29

3-(4-Methylthiophenyl)-4-(4-(methylsulfonyl)phenyl)-2-(5H)-furanone $^1$H NMR (300 MHz, acetone-$d_6$) δ 8.0 (2H, d), 7.70 (2H, d), 7.35 (2H, d), 7.25 (2H, d), 5.35 (2H, s), 3.15 (3H, s), 2.55 (3H, s)

EXAMPLE 30

3-(3-Fluorophenyl)-4-(4-(methylsulfonyl)phenyl)-2-(5H)-furanone $^1$H NMR (300 MHz, $CDCl_3$) δ 7.93 (2H, d), 7.49 (2H, d), 7.35 (1H, m), 7.12 (3H, m), 5.18 (2H, s), 3.06 (3H, s)

EXAMPLE 31

3-(2-Chloro-6-fluorophenyl)-4-(4-(methylsulfonyl)phenyl)-2-(5H)-furanone $^1$H NMR (300 MHz, acetone-$d_6$) δ 8.0 (2H, d), 7.70 (2H, d), 7.55–7.65 (1H, m), 7.40 (1H, d), 7.30 (1H, m), 5.60 (2H, s), 3.15 (3H, s)

EXAMPLE 32

3-(3-Bromo-4-methylphenyl)-4-(4-(methylsulfonyl)phenyl)-2-(5H)-furanone

Analysis calculated for $C_{18}H_{15}BrO_4S$ C, 53.08; H, 3.71 Found: C, 53.06; H, 3.83

EXAMPLE 33

3-(4-Bromo-2-fluorophenyl)-4-(4-(methylsulfonyl)phenyl)-2-(5H)-furanone

Analysis calculated for $C_{17}H_{12}BrFO_4S$ C, 49.65; H, 2.94 Found: C, 49.76; H, 3.00

EXAMPLE 34

3-(3,4-Dibromophenyl)-4-(4-(methylsulfonyl)phenyl)-2-(5H)-furanone $^1$H NMR (300 MHz, acetone-$d_6$) δ 8.0 (2H, d), 7.80 (1H, d), 7.75 (3H, m), 7.25 (1H, d), 5.35 (2H, s), 3.15 (sH, s)

EXAMPLE 35

3-(4-Chloro-3-fluorophenyl)-4-(4-(methylsulfonyl)phenyl)-2-(5H)-furanone

Analysis calculated for $C_{17}H_{12}ClFO_4S$ C, 55.67; H, 3.30 Found: C, 55.45; H, 3.30

EXAMPLE 36

3-(4-Bromo-3-fluorophenyl)-4-(4-(methylsulfonyl)phenyl)-2-(5H)-furanone

Analysis calculated for $C_{17}H_{12}BrFO_4S$ C, 49.66; H, 2.94; S, 7.80 Found: C, 49.7.9; H, 3.01; S, 7.51

EXAMPLE 37

3-(4-Bromo-2-chlorophenyl)-4-(4-(methylsulfonyl)phenyl)-2-(5H)-furanone

Analysis calculated for $C_{17}H_{12}BrClO_4S$ C, 47.74; H, 2.83; S, 7.50 Found: C, 47.92; H, 2.84; S, 7.42

EXAMPLE 38

3-(2-Naphthyl)-4-(4-(methylsulfonyl)phenyl)-2-(5H)-furanone

Analysis calculated for $C_{21}H_{16}O_4S$ C, 69.22; H, 4.43 Found: C, 69.22; H, 4.46

EXAMPLE 39

3-(7-Quinolinyl)-4-(4-(methylsulfonyl)phenyl)-2-(5H)-furanone

Analysis calculated for $C_{20}H_{15}NO_4S$ C, 65.74; H, 4.14; N, 3.83 Found: C, 65.34; H, 4.40; N, 3.80 M.S. (DCI, $CH_4$) calculated for $M^+$, 365 Found for $M^++1$, 366

EXAMPLE 40

3-(3,4-Dichlorophenyl)-4-(4-(aminosulfonyl)phenyl)
-2-(2H)-furanone $^1$H NMR (400 MHz, $CD_3COCD_3$) δ 7.92 (2H, dd), 7.64 (3H, dm), 7.60 (1H, dd), 7.32 (1H, dd), 6.70 (1H, bs), 5.38 (2H, s)

EXAMPLE 41

3-(3,4-Difluorophenyl)-4-(4-(aminosulfonyl)phenyl)
-2-(2H)-furanone $^1$H NMR (400 MHz, $CD_3COCD_3$) δ 7.92 (2H, dd), 7.64 (2H, dd), 7.30–7.45 (2H, m), 7.22 (1H, m), 6.68 (2H, bs), 5.37 (2H, s)

EXAMPLE 42

3-(3-Chloro-4-methoxyphenyl)-4-(4-(aminosulfonyl) phenyl)-2-(2H)-furanone

Analysis calculated for $C_{17}H_{14}ClNO_5S$ C, 53.76; H, 3.72, N, 3.69 Found: C, 53.32; H, 3.84, N, 3.59 M.S. (DCI, $CH_4$) calculated for $M^+$, 379 Found for $M^++1$, 380

EXAMPLE 43

3-(3-Bromo-4-methoxyphenyl)-4-(4-(aminosulfonyl) phenyl)-2-(2H)-furanone

Analysis calculated for $C_{17}H_{14}BrNO_5S$ C, 48.13; H, 3.33, N, 3.30 Found: C, 48.26; H, 3.40, N, 3.28 M.S. (DCI, $CH_4$) calculated for $M^+$, 423 Found for $M^++1$, 424

Assays for Determining Biological Activity

The compound of the instant invention can be evaluated for efficacy by use of one or more of the following assays. As appreciated by those of skill in the art, the efficacy of a compound within the scope of the invention may be determined by statistical comparison of results achieved in the presence of that compound to that which is achieved in it's absence. Alternative may also be utilized

BONE RESORPTION (PIT) ASSAY

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Preparation of bone slices:

Bone slices (20 μm) are obtained by cutting 5 mm sections of bovine bone cylinders taken from bovine femur diaphysis using a low-speed diamond saw (Isomet, Buehler, Ltd., Lake Bluff, Ill.). following by the method of Arnett and Dempster, Endocrinology 120:602–608, 1987.

Slices are cleaned by ultrasonication, 3× in distilled water at 15 mins each. The slices are then rinsed in distilled water and placed in a 96-well plates. The plates are then placed in a tissue culture hood under uv light to sterilize and dry the bone slices. Prior to incubation with osteoclasts, bone slices were rehydrated in 0.1 ml complete medium 199 with 1% antimycotic/antibiotics (GIBCO, New York) and 10% fetal calf serum for 60 min.

Preparation of osteoclasts:

Rat long bones (tibiae, femora, humeri) are obtained from newborn rats (1–3 days old), cleaned of adherent tissue and minced in ice with scalpel blades in 3 ml Medium 199. The resulting suspension was gently pipetted 120 times with a wide-bore pipet and adjusted such that 750 μl of media is utilized for a preparation from one rat. The cell suspension is then filtered through a 100 μm nylon cell strainer (Falcon). The resulting suspension is then aliquoted at 100 μm/well. Finally, 22 μl of a 10× concentration of test drug is added to each well.

Incubation, staining and quantitation of pits:

Osteoclasts and bone slices are incubated for 24 hrs, the bone slices are washed 2× in PBS, then fixed with 2.5% glutaraldehyde/0.1M cacodylate (100 μl/well) for at least 20 mins. The bone slices are then washed for 2× in PBS and sonicated for 2 min in 0.25M $NH_4OH$ at 100 μl/well in order to strip the cells from the lacunae. The bones are subsequently sonicated twice more in distilled water, 15 min each. The bone slices are stained in the wells with 1% toluidine blue/1% sodium borate for 5–7 min. The bone slices are dried and the number of pits are counted by epifluorescence.

OCFORM ASSAY

Osteoblast-like cells (1.8 cells), originally derived from mouse calvaria, are plated in CORNING 24 well tissue culture plates in α MEM medium containing ribo- and deoxyribonucleosides, 10% fetal bovine serum and penicillin-streptomycin. Cells are seeded at 40,000/well in the morning. In the afternoon, bone marrow cells are prepared from six week old male Balb/C mice as follows:

Mice are sacrificed, tibiae removed and placed in the above medium. The ends are cut off and the marrow is flushed out of the cavity into a tube with a 1 mL syringe with a 27.5 gauge needle. The marrow is suspended by pipetting up and down with a glass pasteur pipette. The suspension is passed through two layers of approximately 400 μm mesh stainless steel cloth. The resulting suspension is centrifuged at 350×g for seven minutes. The pellet is resuspended, and a sample is diluted in 2% HOAC to lyse the red cells. The remaining cells are counted in a hemocytometer. The cells are pelleted and resuspended at $1×10^6$ cells/mL. 50 μL is added to each well to yield 50,000 cells/well and 1,25-dihydroxy-vitamin $D_3(D_3)$ is added to each well to a final concentration of 10 nM. The cultures are incubated at 37° C. in a humidified, 5% $CO_2$ atmosphere. After 48 h, the medium is changed. 72 h after the addition of bone marrow, test compounds are added with fresh medium containing $D_3$ to triplicate wells. Compounds are added again after 48 h with fresh medium containing $D_3$. After an additional 24 h the medium is removed, cells are fixed with 10% formaldehyde in phosphate buffered saline for 10 minutes at r.t., followed by a 1–2 minute treatment with EtOH:acetone (1:1) and air dried. The cells are then stained for tartrate resistant acid phosphatase as follows:

The cells are stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates are washed extensively with deonized water and air dried. The number of multinucleated, positively staining cells are counted in each well.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth herein above may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A method of inhibiting bone resorption in a patient in need of such inhibition comprising administration of a non-toxic therapeutically effective amount of a selective cyclooxygenase-2 inhibitor wherein the inhibitor is a compound of Formula Ia

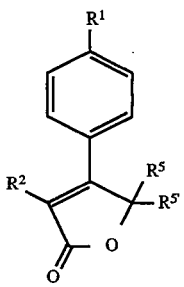

Ia or pharmaceutically acceptable salts thereof wherein:

$R^1$ is selected from the group consisting of
 (a) $S(O)_2CH_3$,
 (b) $S(O)_2NH_2$,
 (c) $S(O)_2NHC(O)CF_3$,
 (d) $S(O)NHCH_3$,
 (e) $S(O)NHNH_2$, and
 (f) $S(O)NHNHC(O)CF_3$;

$R^2$ is selected from the group consisting of
 (a) $C_{1-6}$alkyl,
 (b) $C_3$, $C_4$, $C_5$, $C_6$, and $C_7$, cycloalkyl,
 (c) mono-, di- or tri-substituted phenyl or naphthyl wherein the substituent is selected from the group consisting of selected from the group consisting of
  (1) hydrogen,
  (2) halo,
  (3) $C_{1-6}$alkoxy,
  (4) $C_{1-6}$alkylthio,
  (5) CN,
  (6) $CF_3$,
  (7) $C_{1-6}$alkyl,
  (8) $N_3$,
  (9) —$CO_2H$,
  (10) —$CO_2$—$C_{1-4}$alkyl,
  (11) —$C(R^3)(R^4)$—OH,
  (12) —$C(R^3)(R^4)$—O—$C_{1-4}$alkyl, and
  (13) —$C_{1-6}$alkyl-$CO_2$—$R^3$;
 (d) heteroaryl
 (e) benzoheteroaryl $R^3$, $R^4$, $R^5$ and $R^{5'}$ are each independently selected from the group consisting of
 (a) hydrogen,
 (b) $C_{1-6}$alkyl.

2. A method according to claim 1 wherein $R^1$ is selected from the group consisting of
 (a) $S(O)_2CH_3$, and
 (b) $S(O)_2NH_2$, $R^2$ is mono or di-substituted phenyl wherein the substituents are selected from the group consisting of (1) hydrogen,
 (2) halo, selected from the group consisting of fluoro, chloro and bromo; and $R^5$ and $R^{5'}$ are each hydrogen.

3. A method according to claim 2 wherein the compound of Formula Ia is 3-(3,4-Difluorophenyl)-4-(4-(methylsulfonyl)phenyl)-2-(5H)-furanone, 3-phenyl-4-(4-(methylsulfonyl)phenyl)-2-(5H)-furanone, or a pharmaceutically acceptable salt thereof.

4. A method of preventing, retarding, halting or reversing loss of bone mass in a patient in need of such prevention comprising administration of a non-toxic therapeutically effective amount of a selective cyclooxygenase-2 inhibitor wherein the inhibitor is a compound of Formula Ia

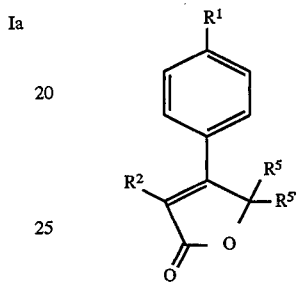

Ia or pharmaceutically acceptable salts thereof wherein:

$R^1$ is selected from the group consisting of
 (a) $S(O)_2CH_3$,
 (b) $S(O)_2NH_2$,
 (c) $S(O)_2NHC(O)CF_3$,
 (d) $S(O)NHCH_3$,
 (e) $S(O)NHNH_2$, and
 (f) $S(O)NHNHC(O)CF_3$;

$R^2$ is selected from the group consisting of
 (a) $C_{1-6}$alkyl,
 (b) $C_3$, $C_4$, $C_5$, $C_6$, and $C_7$, cycloalkyl,
 (c) mono-, di- or tri-substituted phenyl or naphthyl wherein the substituent is selected from the group consisting of
  (1) hydrogen,
  (2) halo,
  (3) $C_{1-6}$alkoxy,
  (4) $C_{1-6}$alkylthio,
  (5) CN,
  (6) $CF_3$,
  (7) $C_{1-6}$alkyl,
  (8) $N_3$,
  (9) —$CO_2H$,
  (10) —$CO_2$—$C_{1-4}$alkyl,
  (11) —$C(R^3)(R^4)$—OH,
  (12) —$C(R^3)(R^4)$—O—$C_{1-4}$alkyl, and
  (13) —$C_{1-6}$alkyl-$CO_2$—$R^3$;
 (d) heteroaryl
 (e) benzoheteroaryl $R^3$, $R^4$, $R^5$ and $R^{5'}$ are each independently selected from the group consisting of
 (a) hydrogen,
 (b) $C_{1-6}$alkyl.

5. A method according to claim 4 wherein $R^1$ is selected from the group consisting of
 (a) $S(O)_2CH_3$, and
 (b) $S(O)_2NH_2$, $R^2$ is mono or di-substituted phenyl wherein the substituents are selected from the group consisting of (1) hydrogen,
(2) halo, selected from the group consisting of fluoro, chloro and bromo; and $R^5$ and $R^{5'}$ are each hydrogen.

6. A method according to claim 5 wherein the compound of Formula Ia is 3-(3,4-Difluorophenyl)-4-(4-(methylsulfonyl)phenyl)-2-(5H)-furanone, 3-phenyl-4-(4-(methylsulfonyl)phenyl)-2-(5H)-furanone, or a pharmaceutically acceptable salt thereof.

7. A method of reducing fractures in a patient in need of such reduction comprising administration of a non-toxic therapeutically effective amount of a selective cyclooxygenase-2 inhibitor wherein the inhibitor is a compound of Formula Ia

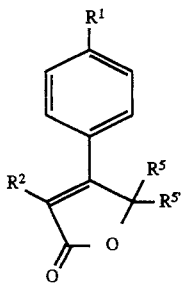

Ia or pharmaceutically acceptable salts thereof wherein:

$R^1$ is selected from the group consisting of
(a) $S(O)_2CH_3$,
(b) $S(O)_2NH_2$,
(c) $S(O)_2NHC(O)CF_3$,
(d) $S(O)NHCH_3$,
(e) $S(O)NHNH_2$, and
(f) $S(O)NHNHC(O)CF_3$;

$R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl or naphthyl wherein the substituent is selected from the group consisting of selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^3)(R^4)$—OH,
(12) —$C(R^3)(R^4)$—O—$C_{1-4}$alkyl, and
(13) —$C_{1-6}$alkyl-$CO_2$—$R^3$;
(d) heteroaryl
(e) benzoheteroaryl $R^3$, $R^4$, $R^5$ and $R^{5'}$ are each independently selected from the group consisting of
(a) hydrogen,
(b) $C_{1-6}$alkyl.

8. A method according to claim 7 wherein $R^1$ is selected from the group consisting of
(a) $S(O)_2CH_3$, and
(b) $S(O)_2NH_2$.

$R^2$ is mono or di-substituted phenyl wherein the substituents are selected from the group consisting of (1) hydrogen,
(2) halo, selected from the group consisting of fluoro, chloro and bromo; and $R^5$ and $R^{5'}$ are each hydrogen.

9. A method according to claim 8 wherein the compound of Formula Ia is 3-(3,4-Difluorophenyl)-4-(4-(methylsulfonyl)phenyl)-2-(5H)-furanone, 3-phenyl-4-(4-(methylsulfonyl)phenyl)-2-(5H)-furanone, or a pharmaceutically acceptable salt thereof.

10. A method of preventing, retarding, halting or reversing osteoporosis in a patient in need of such prevention comprising administration of a non-toxic therapeutically effective amount of a selective cyclooxygenase-2 inhibitor wherein the inhibitor is a compound of Formula Ia

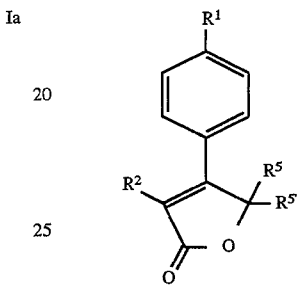

Ia or pharmaceutically acceptable salts thereof wherein:

$R^1$ is selected from the group consisting of
(a) $S(O)_2CH_3$,
(b) $S(O)_2NH_2$,
(c) $S(O)_2NHC(O)CF_3$,
(d) $S(O)NHCH_3$,
(e) $S(O)NHNH_2$, and
(f) $S(O)NHNHC(O)CF_3$;

$R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl or naphthyl wherein the substituent is selected from the group consisting of selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^3)(R^4)$—OH,
(12) —$C(R^3)(R^4)$—O—$C_{1-4}$alkyl, and
(13) —$C_{1-6}$alkyl-$CO_2$—$R^3$;
(d) heteroaryl
(e) benzoheteroaryl $R^3$, $R^4$, $R^5$ and $R^{5'}$ are each independently selected from the group consisting of
(a) hydrogen,
(b) $C_{1-6}$alkyl.

11. A method according to claim 10 wherein $R^1$ is selected from the group consisting of
(a) $S(O)_2CH_3$, and
(b) $S(O)_2NH_2$.

$R^2$ is mono or di-substituted phenyl wherein the substituents are selected from the group consisting of (1) hydrogen,
(2) halo, selected from the group consisting of fluoro, chloro and bromo; and $R^5$ and $R^{5'}$ are each hydrogen.

12. A method according to claim 11 wherein the compound of Formula Ia is
3-(3,4-Difluorophenyl)-4-(4-(methylsulfonyl)phenyl)-2-(5H)-furanone, 3-phenyl-4-(4-(methylsulfonyl)phenyl)-2-(5H)-furanone, or a pharmaceutically acceptable salt thereof.

13. A method of maintaining bone density in a patient in need of such maintenance comprising administration of a non-toxic therapeutically effective amount of a selective cyclooxygenase-2 inhibitor wherein the inhibitor is a compound of Formula Ia

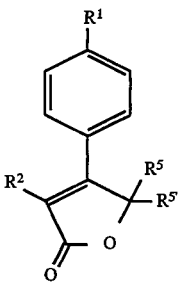

Ia or pharmaceutically acceptable salts thereof wherein:
$R^1$ is selected from the group consisting of
(a) $S(O)_2CH_3$,
(b) $S(O)_2NH_2$,
(c) $S(O)_2NHC(O)CF_3$;
(d) $S(O)NHCH_3$,
(e) $S(O)NHNH_2$, and
(f) $S(O)NHNHC(O)CF_3$;

$R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl or naphthyl wherein the substituent is selected from the group consisting of selected from the group consisting of
(1) hydrogen,
(2) halo,
(3) $C_{1-6}$alkoxy,
(4) $C_{1-6}$alkylthio,
(5) CN,
(6) $CF_3$,
(7) $C_{1-6}$alkyl,
(8) $N_3$,
(9) —$CO_2H$,
(10) —$CO_2$—$C_{1-4}$alkyl,
(11) —$C(R^3)(R^4)$—OH,
(12) —$C(R^3)(R^4)$—O—$C_{1-4}$alkyl, and
(13) —$C_{1-6}$alkyl-$CO_2$—$R^3$;
(d) heteroaryl
(e) benzoheteroaryl $R^3$, $R^4$, $R^5$ and $R^{5'}$ are each independently selected from the group consisting of
(a) hydrogen,
(b) $C_{1-6}$alkyl.

14. A method according to claim 11 wherein
$R^1$ is selected from the group consisting of
(a) $S(O)_2CH_3$, and
(b) $S(O)_2NH_2$, $R^2$ is mono or di-substituted phenyl wherein the substituents are selected from the group consisting of
(1) hydrogen,
(2) halo, selected from the group consisting of fluoro, chloro and bromo; and $R^5$ and $R^{5'}$ are each hydrogen.

15. A method according to claim 14 wherein the compound of Formula Ia is
3-(3,4-Difluorophenyl)-4-(4-(methylsulfonyl)phenyl)-2-(5H)-furanone, 3-phenyl-4-(4-(methylsulfonyl)phenyl)-2-(5H)-furanone, or a pharmaceutically acceptable salt thereof.

* * * * *